United States Patent
Sanfeliu Cortes et al.

(10) Patent No.: US 6,216,432 B1
(45) Date of Patent: Apr. 17, 2001

(54) METHOD FOR INSPECTING SPINNING BOBBINS AND SYSTEM FOR IMPLEMENTING SUCH METHOD

(75) Inventors: Albert Sanfeliu Cortes; Antoni Llorens Castello, both of Barcelona (ES)

(73) Assignee: Cognivision Research, S.L., Barcelona (ES)

( * ) Notice: Subject to any disclaimer, the term of this patent is extended or adjusted under 35 U.S.C. 154(b) by 0 days.

(21) Appl. No.: 09/197,089

(22) Filed: Nov. 19, 1998

Related U.S. Application Data

(63) Continuation of application No. PCT/ES97/00070, filed on Mar. 19, 1997.

(51) Int. Cl.[7] .................................................. D01H 7/46
(52) U.S. Cl. ........................ 57/264; 57/265; 250/559.07; 250/559.4; 250/559.46
(58) Field of Search ................ 57/264, 265; 250/559.07, 250/559.08, 559.4, 559.45, 559.46; 356/237.1, 238.1, 238.2

(56) References Cited

U.S. PATENT DOCUMENTS

| | | | |
|---|---|---|---|
| 4,866,289 | * 9/1989 | Kawamura et al. | 250/572 |
| 5,138,151 | * 8/1992 | Inada et al. | 250/223 R |
| 5,315,366 | * 5/1994 | Inada et al. | 356/238 |
| 5,337,138 | * 8/1994 | Inada et al. | 356/36 |
| 5,359,408 | * 10/1994 | Inada et al. | 356/238 |
| 5,636,803 | * 6/1997 | Aschmann et al. | 424/36 |
| 5,815,198 | * 9/1998 | Vachtsevanos et al. | 348/88 |

\* cited by examiner

*Primary Examiner*—William Stryjewski
(74) *Attorney, Agent, or Firm*—Graybeal Jackson Haley LLP

(57) ABSTRACT

The method which is applicable to the inspection of bobbins of yarn of any size, color and material, is based on the acquisition of images of the surface of the bobbin and on their processing by a computer program in order to evaluate defects, and comprises various steps of exploring the bobbin (1) taking a plurality of images of various areas of said bobbin, each step occurring under specific conditions of lighting and relative position of particular image sensors (3, 4) in order to identify specific defects, displacing either the bobbin (1) or the image acquisition device (3, 4), or bot to explore, sector by sector, the whole surface of interest, each of the focused images, related to a particular defect being processed individually by the evaluation program.

14 Claims, 7 Drawing Sheets

METHOD FOR INSPECTING SPINNING BOBBINS AND SYSTEM FOR IMPLEMENTING SUCH METHOD

This application is a continuation of PCT/ES97/00070 filed on Mar. 19, 1997.

FIELD OF INVENTION

This invention relates to a method for inspecting spinning bobbins and system for implementing such methods.

The method and system according to the invention are applied to scanning yarn bobbins after their winding process on a core which gives rise to one or more stations embedded in a conveyor line for said recently formed bobbins carriage towards a point of use or storage. The method and system proposed are adapted for processing bobbins having different sizes, colours and materials, comprising a step for acquiring (capturing and lighting) images on the bobbin surface, a second step of processing said images through digitizing and an end process by means of an analysis computer program applied to withdraw and assess the defects.

The system according to the invention allows to detect a great number of defects which can appear on the spinning bobbins and namely, broken filaments, loops, webbing, scratching or defibered parts and blows, stains on the bobbin end faces and on its sides, scratching, blows and unevenness, deformations, cavings and bobbin density, tube colour and yarn butt end as well as circles or stains on the bobbin end faces. The system is based on a generally sequential and matched action of a plurality of image acquiring sensors, several of which are moveable in order to be able to locate them at predetermined points before starting each cycle of image capture of a related detection or scanning step, generally specific for each of the defects and in which a while bobbin area is scanned, sector by sector, and the images acquired are also processed one by one or integrated with other images corresponding to a scanning step. At each of said detection steps a lighting has been provided specially adapted to each case whose arrangement, matched with a suitable optics, provides a sufficient field depth effect in order that the defects present in the sector are perfectly focused in resulting image.

BACKGROUND OF THE INVENTION

Several embodiments are known in the state of the art which are applied to detect defects in yarn bobbins.

Japanese patent application 62-62938 and U.S. Pat. No. 5,138,151 disclose methods for detecting based on sensors for acquiring image by line by line reading, provided to give rise to a station embedded in a line to transfer bobbins toward a storage or service area.

This prior art methods have the main drawback that for localizing a defect it requires two or three acquisitions of the image sensor, its use meaning in addition limitations as for the bobbin colour and/or material, which make the general use of this method difficult which is mainly useful for direct reflection bobbins. In addition, as this kind of sensors only read one line, the encompassed field is then very restricted and the shots have to be performed at points very near to achieve effective results.

On the other hand, Japanese patent application 134105 and U.S. Pat. No. 5,359,408 disclose devices for inspecting spinning bobbins comprising a matrix type camera image acquisition means, the later of these background disclosing arrangements applied for detecting different defects with the use of several types of lighting sources such as ultraviolet rays, fluorescent or other.

However in said prior art patents the possibility is not contemplated to perform a complete scanning of all the bobbin surfaces, carrying out an inspection of multiple and different defects, which occurs in some cases twice or more times and by means of one or two stations embedded in a conveyor line of recently produced bobbins with the peculiarity that it is adaptable to different bobbin sizes and regardless the bobbin colour and material characteristics be.

There are not either disclosed in the state of the art the series of arrangements relative to image acquisition sensors and lighting sources this invention proposes and which namely provides with an effect of field depth such it allows to accurately focus the defects at each scanned sector which significantly facilitates their identification.

BRIEF SUMMARY OF THE INVENTION

Essentially the method according to the invention is based on several bobbin scanning steps, shooting at each step a plurality of images from different areas of a bobbin to be inspected, in general sequentially and at each step under particular lighting conditions and with a definite position of several specific, i.e. distinct image acquisition sensors provide to facilitate for each of said lighting conditions and definite positions of said specific sensor and identification-withdrawal of some special defects to be detected, moving accordingly either said bobbin or said image acquisition sensors or both to scan, sector by sector, a whole surface of interest. According to said method, it is in addition operated in every case under field depth conditions so that they make possible to correctly focus the defects present in a related sector, and each of the focused images associated to a particular defect or group of defects is likewise processed in a single way or integrated with other images corresponding to a scanning step obtained through the same image acquisition sensor, by an assessing program, depending on an specific defect to determine and regardless of the size, colour or material of said bobbin.

According to this method, inspecting bobbin end faces is achieved by image acquisition by means of at least three different arrangements of the image acquisition sensors and lighting sources to be used, two of the sensors on the sides and a third one located above the bobbin end faces, with the peculiarity that the side sensors are moveable, moving in parallels to the bobbin shaft to cover end faces defects and on its side wall by automatically governed driving means operation.

As for the system, it comprises one or several working stations which include a plurality of image acquisition sensor such as a matrix camera, with at least one image sensor above each end face, with it optical axis approximately parallel to the bobbin shaft, but moved sideways with respect thereof and other image sensors installed associated to columns parallel to the bobbin winding shaft with their optical axis oriented perpendicular to said bobbin and moveable along said columns in order to be poisoned level or slightly above each of the end faces or covering the bobbins side area. In addition this system includes means to rotate the bobbin at constant speed in order to make workable a sequential shot of a plurality of images thereof and comprising in addition a plurality of lighting sources associated one by one to related image sensors and if fit moveable with same, or fixed, operating individually jointly with one determined of the image sensors and with specific spatial orientations.

BRIEF DESCRIPTION OF THE DRAWINGS

For a better understanding, the invention will now be described in a non-limiting way, with reference to the accompanying drawings, in which.

In the following figures the arrangements of the image acquisition means and lighting sources are shown open by one, depending on the defect to be detected on a yarn bobbin.

Figure 3A:
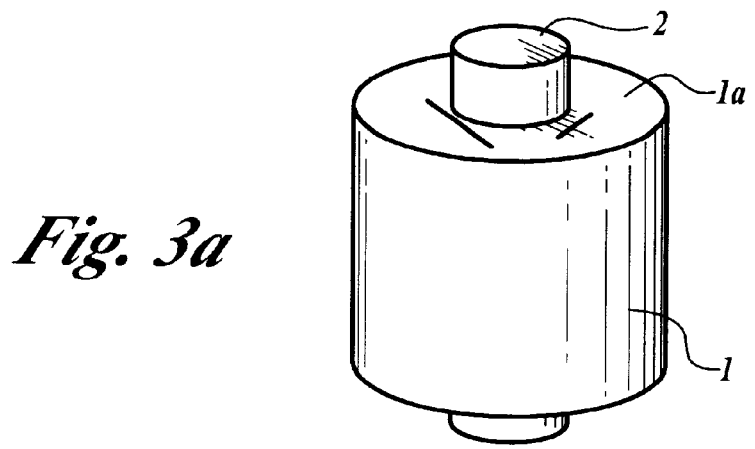
Figure 3B:
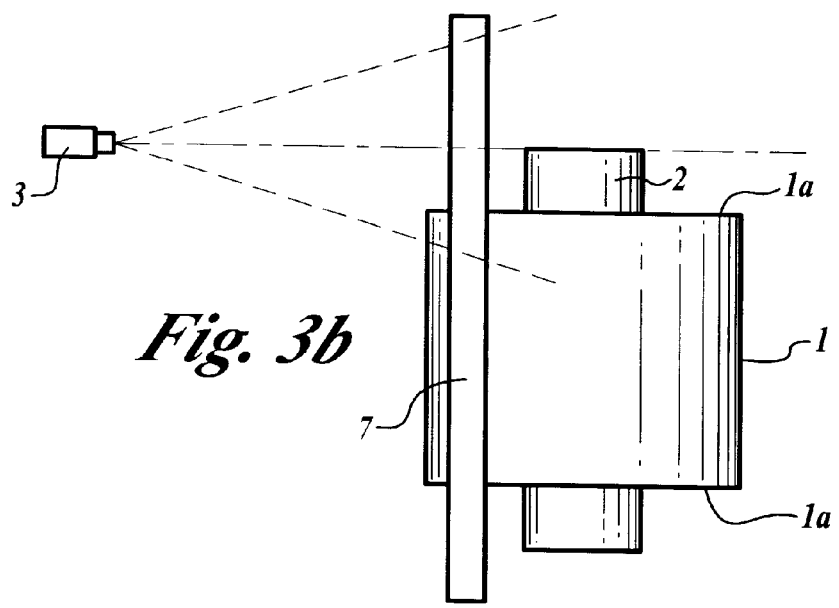
Figure 3C:
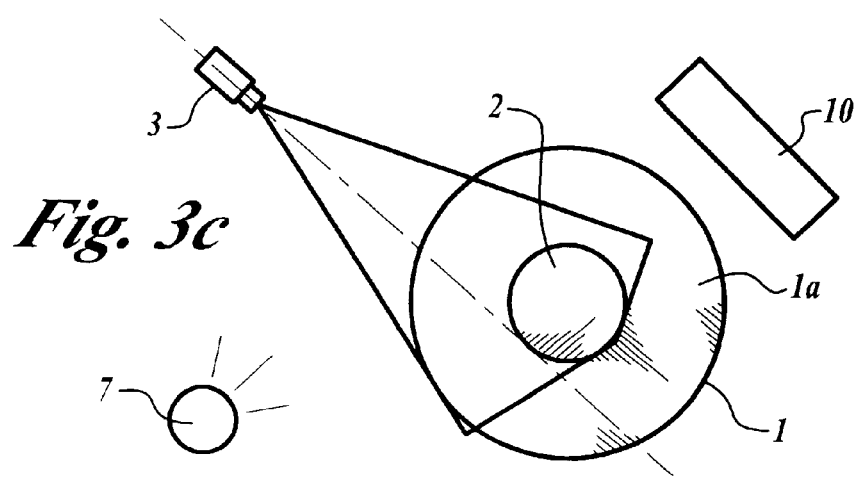

Thus, FIG. 3a shows a bobbin, and it is indicated that on its top face there exists webbing and FIGS. 3b and 3c show a side elevation and plan view, respectively of the image acquisition sensor and lighting sources arrangements used in this case according to the system proposed. In the event of FIG. 3c an alternative arrangement of the lighting source has been also shown.

Figure 4A:
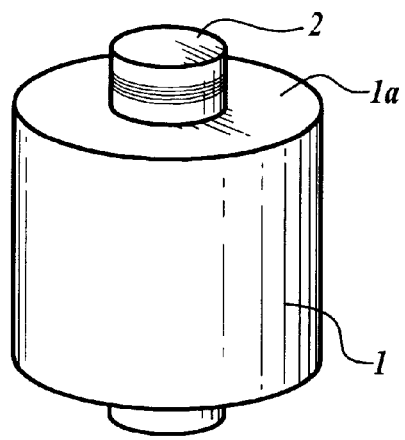
Figure 4B:
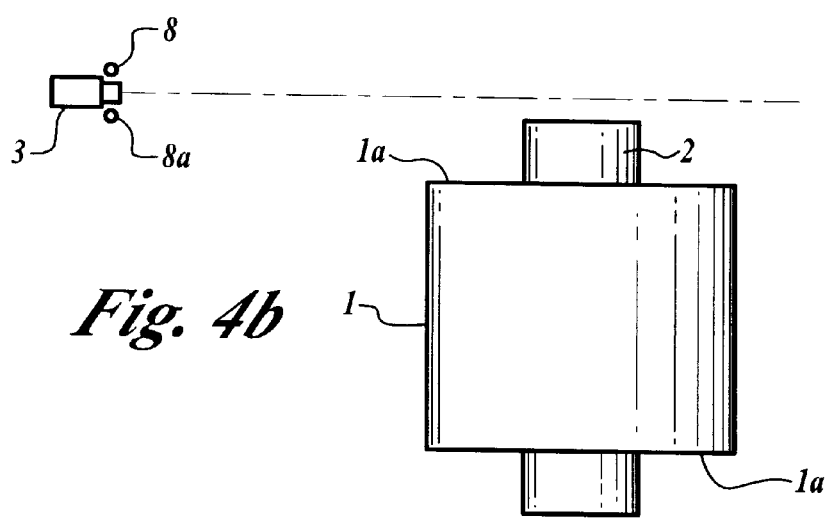
Figure 4C:
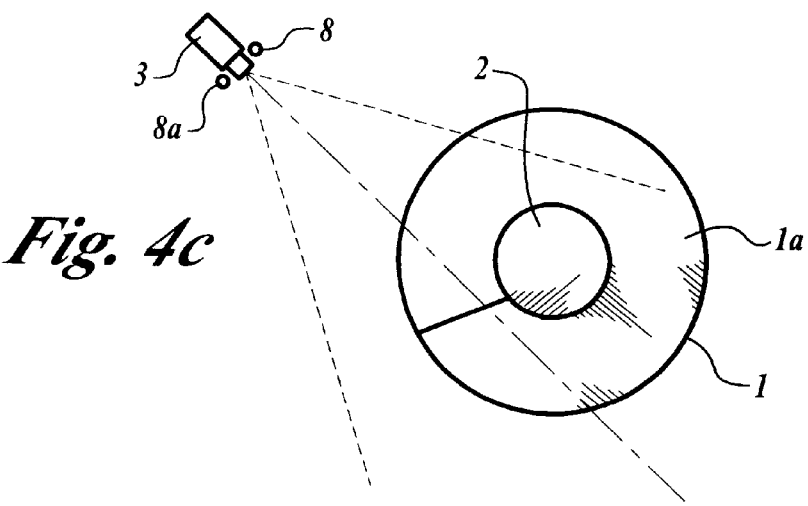

FIG. 4a is a perspective view of a bobbin in which, on the top portion of the winding core protruding from the bobbin a yarn butt end is emphasized and FIGS. 4b and 4c show in a side elevation and plan view the image acquisition sensor and lighting source arrangement used to detect this defect according to the system proposed.

Figure 5A:
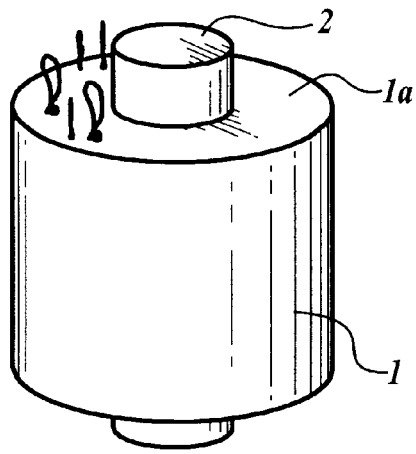
Figure 5B:
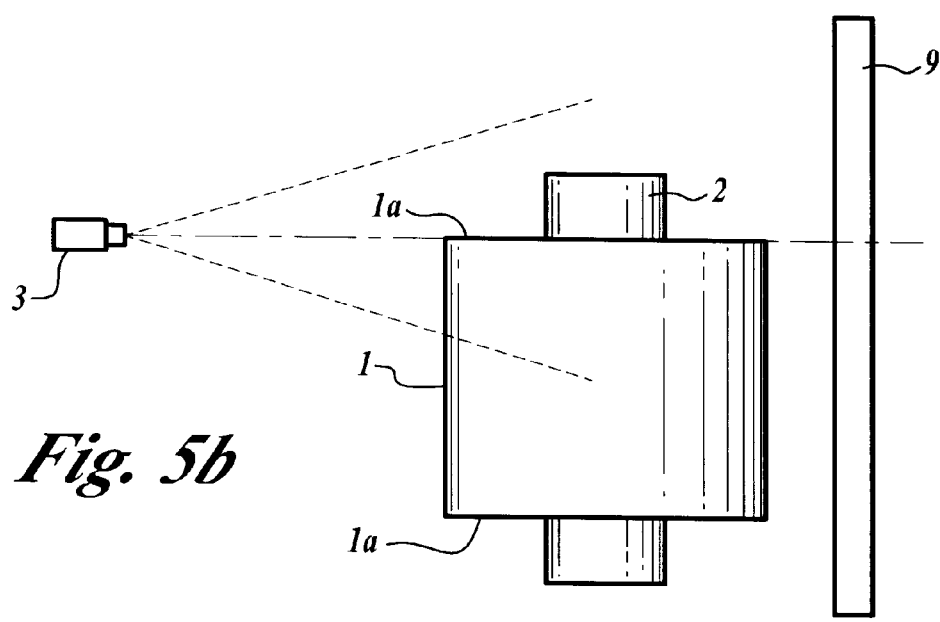
Figure 5C:
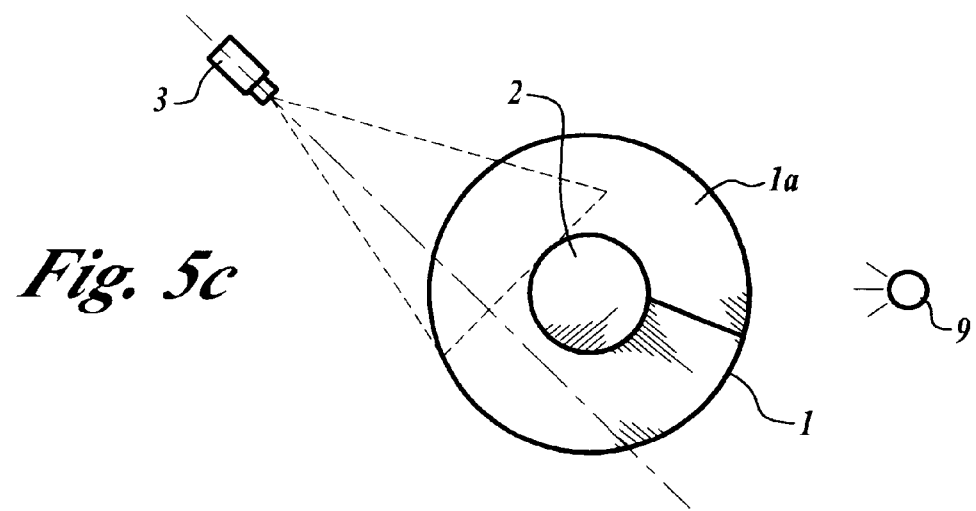

FIG. 5a shows in perspective a bobbin which at its top face shows loop and broken filaments and FIGS. 5b and 5c shown in side elevation and plan view the image acquisition sensor and lighting source arrangement used according to the system proposed. It must be emphasized in addition that inspecting tasks detailed in FIGS. 3a to 5c can be carried out by a same sensor or matrix camera as those shown in FIG. 1, conveniently moving the camera involved along the supporting column with suitable driving means, automatically controlled.

Figure 6A:
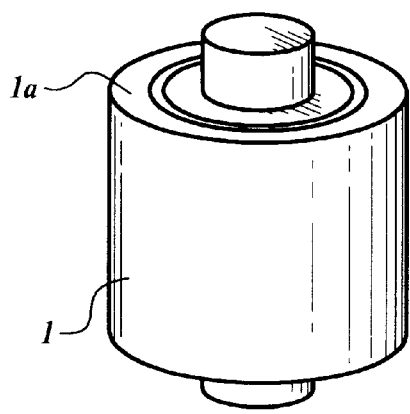
Figure 6B:
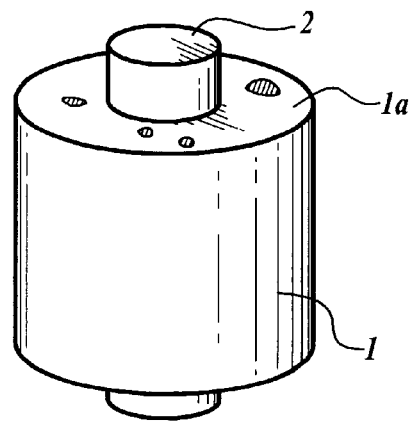
Figure 6C:
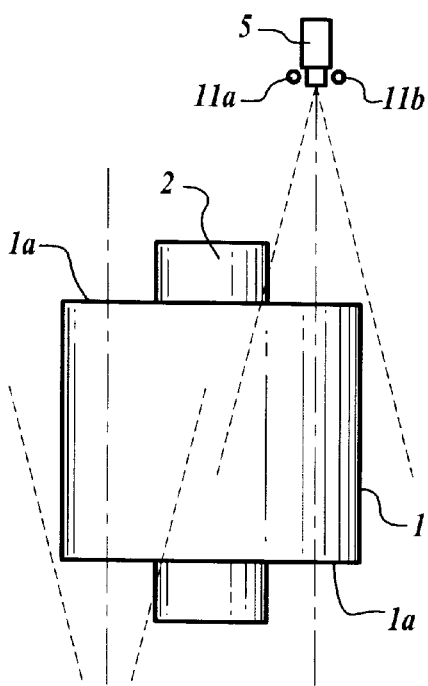
Figure 6D:
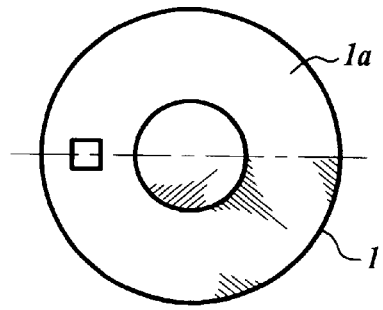

In FIGS. 6a and 6b the bobbins are drawn in perspective which in their top face show circles or stains, respectively, the image acquisition sensor and lighting sources related arrangements for inspecting according to the invention being illustrated in elevation and plan view in FIGS. 6c and 6d.

Figure 7A:
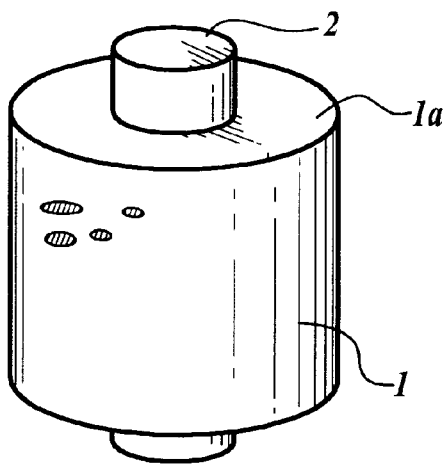
Figure 7B:
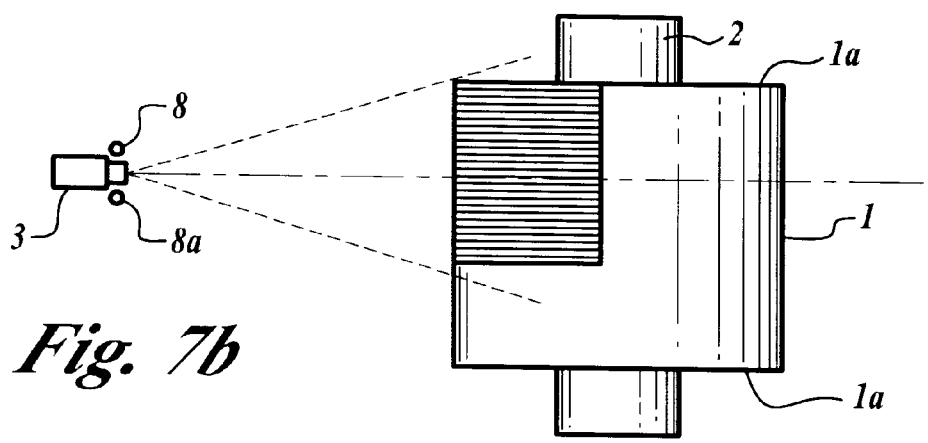
Figure 7C:
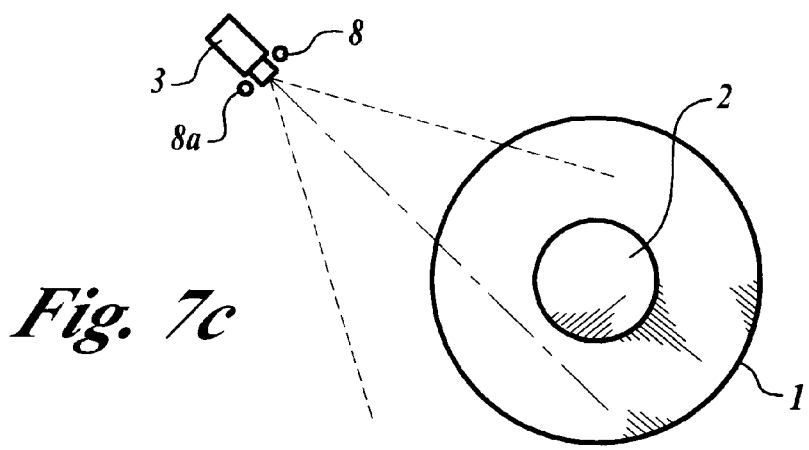

FIG. 7a shows a drawing in perspective of a bobbin with some stains on its side surface. FIGS. 7b and 7c showing the image acquisition sensor and lighting source arrangements used for inspecting this particular defect. The camera used can be same as the one used for inspecting defects of FIGS. 3a to 5c, with a convenient moving and use of specific lighting means.

Figure 8A:
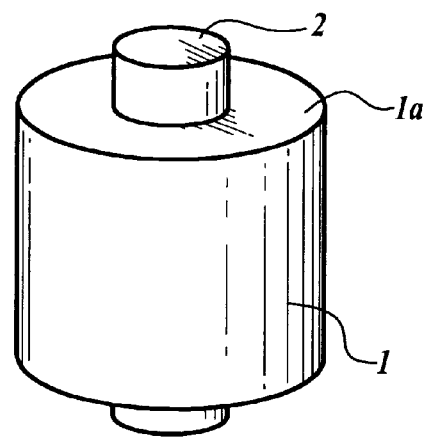
Figure 8B:
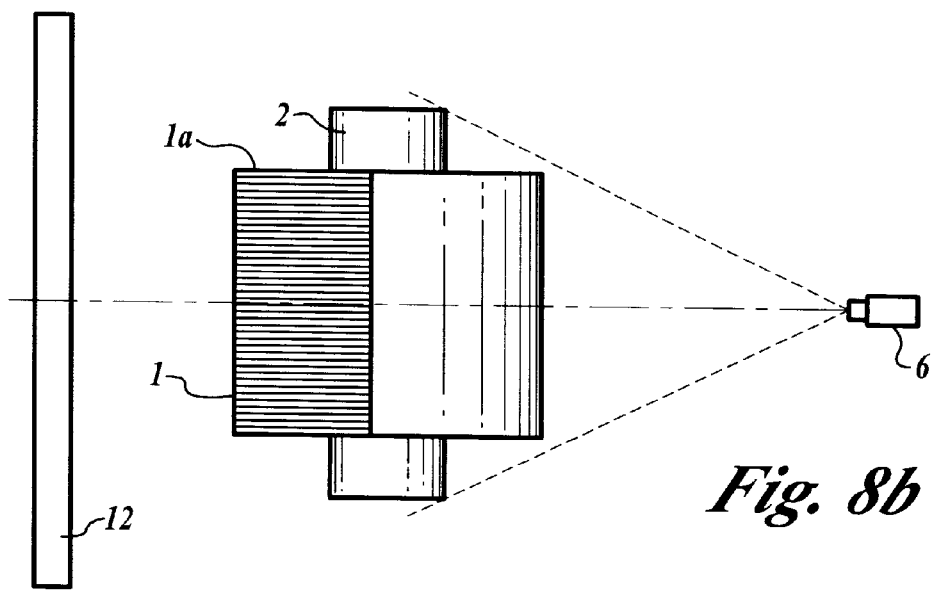
Figure 8C:
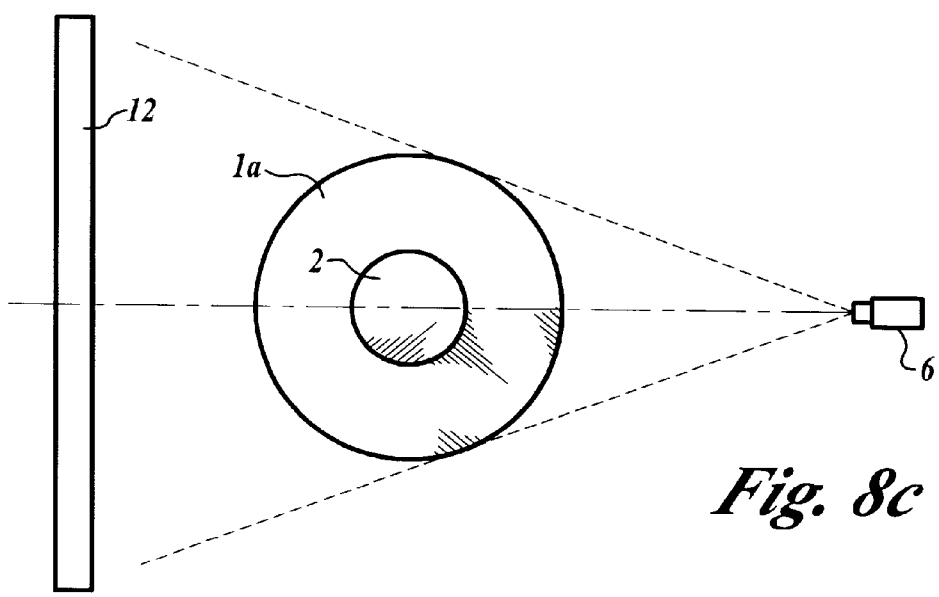

At last, FIG. 8a shows in perspective a bobbin with deformations of its body and FIGS. 8b and 8c show the image acquisition sensor and lighting source arrangement used to assess this defect.

DETAILED DESCRIPTION OF THE INVENTION

Figure 1:
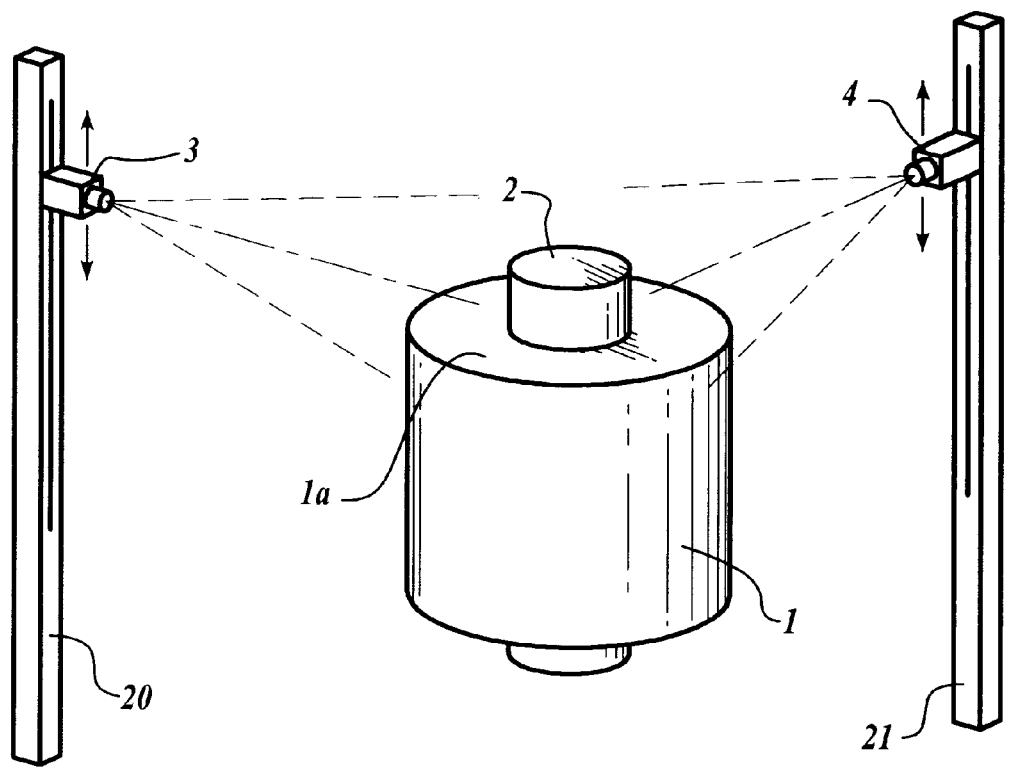
FIG. 1 schematically shows the arrangement of two matrix cameras associated to side columns in order to encompass the bobbin end face or a part or the whole of its side surface. In general, each column will have available at least one of said cameras to simultaneously scan the bobbin end faces and adjacent areas.

According to FIG. 1, the system comprises two side columns 20, 21 in which two image sensors 3, 4 such as a matrix camera are located, designed to cover the bobbin top and lower end faces 1a, which sensors can be moved by suitable electromechanical means along said columns 20, 21 in order to also focus a bobbin side strip 1, and bobbin end faces 1a.

Figure 2:
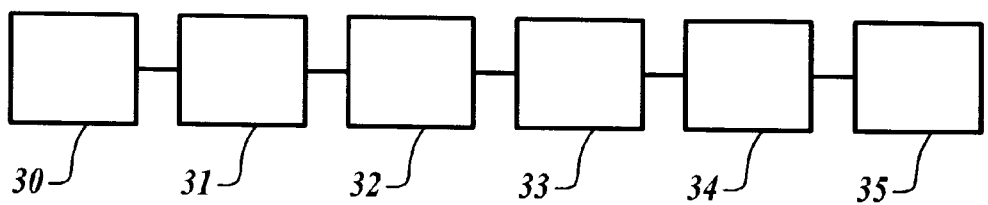
FIG. 2 is a block diagram of the means for acquiring and treating the images captured by said matrix cameras and which comprises a processing and signal analysis circuit and an associated program for processing corresponding images.

FIG. 2 schematically shows an operation diagram of the means for processing each of the images comprising an image acquisition block 30, a block for improving said image 31, a filtering step 32, a binarization step 33 of the image, a block for extracting characteristics 34 and a final classification step 35. Each of the images acquired are converted into two-colour digital images and from said two-colour image elements those geometrical characteristics particular for each defect are withdrawn, which compared against preestablished determined values stored in memories allow to assess whether a defect is existing or not.

The system comprises, for detecting broken filaments, loops or other protrusions or bulging from the surface of one of the bobbin ends 1a or scratches, i.e. defibered parts as shows FIG. 5a, an image sensor 3 whose optical axis is approximately parallel to the plane defined by the bobbin end face 1a and is arranged approximately level with said face and an elongated lighting source 9 for adapting bobbin different lengths located in a sector comprised between 135 and 180 degrees, clockwise far away with respect to said image sensor 3 so that reflection is helped and said image sensor blinding is prevented said lighting cooperating in a suitable focus for detecting defects in the sector.

According to the explained system, the same image sensor 3 applied to detect broken filaments and loops can be operated in order to detect webbing, scratches and blows, on bobbin end faces 1a, whose detecting step is shown in FIGS. 3a to 3c for which said sensor 3 optical axis is displaced in elevation with respect to the plane defined by the bobbin end face 1a so that all said end face remains always visible in the field of view and in that an elongated lighting source 7 is used, having a development parallel to the bobbin shaft 2, for adapting it to several lengths, located in a sector between 270 to 350 degrees far away, clockwise, with respect to said image sensor 3, 4 preventing blinding it and helping the light reflecting from the defect to be detected.

FIG. 3c shows an alternative lighting source 10 also suitable for detecting webbing, located within a sector about 45 to 90 degrees far away, clockwise, elongated but parallel to one of the bobbin end faces 1, 1a with a screening such to allow a beam of light projection following a plane with an about 30 degrees slope above the one corresponding to the bobbin end face 1, 1a.

FIGS. 4a to 4c shows the butt end yarn and winding core colour protruding from the bobbin by its ends detection step for which same image sensor 3 is used as for detecting webbing which has incorporated in this case a lighting source 8, 8a arranged behind the lends of said image acquisition sensor in order it produces an image by reflected light.

The bobbin side stains and unevenness or bulging occurring on side surface 1 are detected by means of at least one of the image acquisition sensor 3, 4 applied to cover the bobbin two end faces 1a conveniently displaced along the columns 20, 21 to focus on the area of interest whose location has been illustrated in FIGS. 7a to 7c.

Lighting source 8, 8a located behind the sensor lens provided the desired illumination.

In FIGS. 6a to 6d, it can be seen that each of the image acquisition sensors 5, 5a located above the bobbin end faces 1a has available a lighting source 11a, 11b located behind the senor lens and which allows to detect circles and stains in said two faces as well as to detect webbing which cannot be detected with specific means applied to their detection.

In FIGS. 8a to 8c an additional image detection sensor 6 has been shown which allows to capture the complete bobbin image 1, 1*a* with a suitable resolution, providing a focusing and field depth such that the bobbin outline is detected by contrast of it with respect to a lighting source 12, opposed located behind said bobbin, allowing to calculate bobbin sizes and density, as well as determining the bobbin cavings and deformations.

What is claimed is:

1. A method for inspecting spinning bobbins having a shaft or winding tube, a side face, an upper end face and a lower end face comprising
    a) acquiring at a single station a plurality of images including bobbin side and end faces under known lighting conditions using a plurality of image acquisition sensors having known positions relative to said bobbin at the time of image acquisition;
    b) moving either said bobbin or said plurality of image acquisition sensors or both to scan a whole surface of interest in order to identify a particular possible defect or group of defects; and
    c) processing said acquired images individually or collectively with an assessing program to determine the presence or absence of said particular defect or group of defects.

2. The method of claim 1 wherein the plurality of image acquisition sensors comprises at least one sensor directed to said upper bobbin and face, at least one sensor directed to said lower bobbin end face, and at least one sensor directed to said bobbin side face and wherein said at least one sensor directed to said bobbin side face is moveable with respect to said bobbin.

3. The method of claim 2 wherein the bobbin is rotated at a constant speed and during said rotation and synchronically one or a predetermined number of images are acquired by each of said image acquisition sensors, so that a whole face, surface or part of the bobbin to be inspected is imaged and, concurrently therewith either an independent processing of each image or an integration of a particular sequence of images is undertaken to determine the presence or lack of a type of defect.

4. The method of claim 3 wherein sequential simultaneous images of the bobbin two end faces are obtained.

5. A system for inspecting spinning bobbins having a shaft or winding tube, a side face, an upper end face and a lower end face comprising:
    a first and a second column located parallel to the bobbin shaft (2), which having translationally mounted thereon a respective first and second image sensor so that the optical axis of the first and second image sensor is oriented perpendicularly to said bobbin and moveable by driving means along said columns in order to be positioned, approximately level or slightly above each of the end faces or covering partly or completely, the bobbin side face; and
    means to rotate the bobbin.

6. The system of claim 5 further comprising a third image sensor located above the upper bobbin end face and a fourth image sensor located below the lower bobbin end face, the optical axis of the third and fourth image sensors being parallel to, but not coaxial with the bobbin shaft.

7. The system of claim 6 wherein each images acquisition sensors has a lens and a lighting source located behind the sensor lens.

8. The system of claim 5 wherein the optical axis of the first and second image sensors are approximately parallel to the plane defined by the bobbin end face and arranged approximately level to said face, and further comprising a light source located in a sector ranging from about 135 to 180 degrees, clockwise far away with respect to the straight line which joins at least the first image sensor with a bobbin shaft, in such a way it helps the reflection and prevents blinding said image sensor.

9. The system of claim 8 wherein the optical axis of said first and second sensors are moved beyond the plane which defines a bobbin end face, so that in the field of view said end face remains always available for imaging and wherein the light source is located within a sector clockwise ranging from about 270 to 350 degrees far away, with respect to the straight line formed by at least the first image sensor and the bobbin shaft.

10. The system of claim 9 further comprising an alternative lighting sources, located within a sector clockwise 45 to 90 degrees far away from the plane formed by at least the first sensor and the bobbin shaft and having a screening to permit the projection of a light beam following a plane with an about 30 degree slope above the corresponding bobbin end face.

11. The system of claim 9 further comprising a lighting source positioned behind a lens of said first image acquisition sensor.

12. The system of claim 5 wherein at least the first image acquisition sensor is positioned by displacement along a column so as possibly acquire at least one image of at least one bobbin end face.

13. The system of claim 5 further comprising an auxiliary image detection sensor to capture a complete bobbin image with a suitable resolution and bobbin outline to provide data used to calculate the bobbin density and to determine the cavings and deformations thereof.

14. The system of claim 5 further comprising means for processing an acquired image or groups of images, means for improving side image or images, and means for converting the image or images into a digital image in two colours, except in the event of step involving a colour detection of the bobbin shaft, from which a comparison is made against pre-established data to determine whether a defect exists or not.

\* \* \* \* \*